United States Patent
Ozaki et al.

(10) Patent No.: US 6,797,782 B2
(45) Date of Patent: Sep. 28, 2004

(54) PROCESS FOR PRODUCING PARTICLES FOR DIAGNOSTIC REAGENT

(75) Inventors: Ichiro Ozaki, Tokyo (JP); Satoshi Katayose, Tokyo (JP); Mikio Hikata, Tokyo (JP); Kejun Fan, Tokyo (JP); Mitsuhiro Murata, Tokyo (JP)

(73) Assignee: JSR Corporation, Tokyo (JP)

( * ) Notice: Subject to any disclaimer, the term of this patent is extended or adjusted under 35 U.S.C. 154(b) by 0 days.

(21) Appl. No.: 10/392,891

(22) Filed: Mar. 21, 2003

(65) Prior Publication Data

US 2003/0181606 A1 Sep. 25, 2003

(30) Foreign Application Priority Data

Mar. 25, 2002 (JP) ........................................ 2002-083733
Oct. 29, 2002 (JP) ........................................ 2002-314730

(51) Int. Cl.$^7$ .......................... C08F 222/10; B05D 1/42
(52) U.S. Cl. ...................... 525/244; 525/245; 525/246; 525/95; 525/91; 525/319; 524/431; 427/475
(58) Field of Search ................... 525/244, 245, 525/246, 95, 91, 319; 524/431; 427/475

(56) References Cited

U.S. PATENT DOCUMENTS

| | | | | |
|---|---|---|---|---|
| 4,554,088 A | * | 11/1985 | Whitehead et al. ...... | 252/62.54 |
| 4,654,267 A | * | 3/1987 | Ugelstad et al. ............ | 428/407 |
| 5,091,206 A | * | 2/1992 | Wang et al. ................ | 427/2.18 |
| 5,320,944 A | * | 6/1994 | Okada et al. ............... | 435/7.94 |
| 5,648,124 A | * | 7/1997 | Sutor .......................... | 427/475 |
| 5,684,130 A | * | 11/1997 | Sucholeiki .................. | 530/333 |
| 5,736,349 A | * | 4/1998 | Sasaki et al. ............... | 435/7.94 |
| 5,814,687 A | | 9/1998 | Kasai et al. | |
| 6,133,047 A | * | 10/2000 | Elaissari et al. ............ | 436/526 |
| 2001/0014468 A1 | * | 8/2001 | Muller-Schulte ............ | 435/181 |

FOREIGN PATENT DOCUMENTS

| EP | 0 344 270 | 12/1989 |
|---|---|---|
| WO | WO 89/04373 | 5/1989 |

* cited by examiner

*Primary Examiner*—Satya B. Sastri
(74) *Attorney, Agent, or Firm*—Oblon, Spivak, McClelland, Maier & Neustadt, P.C.

(57) ABSTRACT

A process of producing particles for diagnostic reagent, including a step of polymerizing a polymerizable monomer in the presence of a matrix particle having a magnetic substance layer containing at least one of $Fe_2O_3$ and $Fe_3O_4$ on the surface thereof and having a mean particle size of 0.4–200 μm to form a polymer layer on the magnetic substance layer.

12 Claims, No Drawings

PROCESS FOR PRODUCING PARTICLES FOR DIAGNOSTIC REAGENT

FIELD OF THE INVENTION

The present invention relates to a process for producing a carrier for diagnostic reagent in biochemical and medicinal fields.

DESCRIPTION OF THE RELATED ART

A method in which a magnetic substance is dispersed in a monomer, the dispersion is subjected to suspension polymerization or miniemulsion polymerization to incorporate the magnetic substance into particles, and the particles are further classified is known as a method for producing particles having a comparatively uniform particle size distribution and capable of compositing a magnetic substance. However, according to this method, the particle size distribution of the particles obtained after completion of the polymerization is very broad, so that the desired uniform particle size cannot be obtained unless a plural number of classification operations are repeated. Further, repeating the classification results in reduction of the yield, leading to failure in balance between the working efficiency and the yield. Moreover, a method in which an iron salt is neutralized, and the resulting iron hydroxide is deposited on porous particles having $NH_2$ and $NO_2$ groups and oxidized is proposed as a method of depositing a metallic compound on particles in water (JP-B-5-10808). However, this method is extremely complicated in terms of the production step, and hence, was not suitable for the mass production. In addition, there is proposed a method of utilizing heterocoagulation (U.S. Pat. No. 5,648,124). However, according to this method, it is difficult to control the coagulation during the addition of a substance having an opposite charge. Further, since compositing is preferentially performed, in many cases, a coagulation reaction excessively takes place. Accordingly, the resulting particles form a coagulated body to an extent such that re-dispersion is difficult and fail in uniformity of the particle size. In addition, there is proposed a method in which a monomer and a magnetically responsible metal oxide are simultaneously polymerized on the surfaces of polymer core particles, to introduce a magnetic substance into the polymer particles (Japanese Patent No. 2,736,467). However, according to this method, the particles after the introduction of a magnetic substance take a structure where they are not completely polymer-coated, and the magnetic substance is present on the particle surfaces. Accordingly, this method involved problems such as falling off of the magnetic substance and elution of substances derived from magnetic components such as an iron ion. It is known that such problems bring adverse influences especially when the particles are used for a carrier for diagnostic reagent. It is reported that in the enzyme immunoassay (EIA) as an analytical method in the biochemical field, in the case where a certain chromogenic substrate such as o-phenylenediamine (OPD) is used for the assay, Fe functions as an interferent and pushes up a background of the assay, thereby causing an error in the assayed values (Rev. Esp. Fisiol., 45(1), 41–46, 1989). Thus, magnetic particles, on the surfaces of which is not present a magnetic substance, and which are free from problems such as falling off of a magnetic substance and elution of an iron ion and can be utilized as a carrier for diagnostic reagent in the EIA, etc., have been demanded.

SUMMARY OF THE INVENTION

An object of the invention is to simply and effectively prepare particles for diagnostic reagent, which are free from falling off of a magnetic substance and elution of substances derived from a magnetic component such as an iron ion and which have a uniform particle size.

Specifically, the invention provides a process for producing particles for diagnostic reagent, which comprises a step of polymerizing a polymerizable monomer in the presence of a matrix particle having a magnetic substance layer containing at least one of $Fe_2O_3$ and $Fe_3O_4$ on the surface thereof and having a mean particle size of 0.4–200 µm to form a polymer layer on the magnetic substance layer.

DETAILED DESCRIPTION OF THE INVENTION

The matrix particle used in the invention is a particle having a magnetic substance layer containing at least one of $Fe_2O_3$ and $Fe_3O_4$ on the surface of a nuclear particle.

The nuclear particle that is used in the invention is basically a non-magnetic substance, and any of organic substances and inorganic substances can be used and can be appropriately selected depending on the purpose of use of particles for diagnostic reagent and so on.

Representative examples of the organic substance include polymers. Vinyl-based polymers are particularly preferable as such polymers. Examples of vinyl-based monomers that are used for the production of vinyl-based polymers include aromatic vinyl monomers such as styrene, α-methylstyrene, halogenated styrenes, and divinylbenzene; vinyl esters such as vinyl acetate and vinyl propionate; unsaturated nitriles such as acrylonitrile; and ethylenically unsaturated carboxylic acid alkyl esters such as methyl acrylate, ethyl acrylate, ethyl methacrylate, butyl acrylate, butyl methacrylate, 2-ethylhexyl acrylate, 2-ethylhexyl methacrylate, lauryl acrylate, lauryl methacrylate, ethylene glycol diacrylate, ethylene glycol dimethacrylate, cyclohexyl acrylate, and cyclohexyl methacrylate. This vinyl-based polymer may be a homopolymer or a copolymer of two or more monomers selected from the above vinyl-based monomers. Copolymers of the vinyl-based monomer with a conjugated diolefin (such as butadiene or isoprene) or a copolymerizable monomer (such as acrylic acid, methacrylic acid, acrylamide, methacrylamide, diglycidyl acrylate, glycidyl methacrylate, N-methylolacrylamide, N-methylolmethacrylamide, 2-hydroxyethyl acrylate, 2-hydroxyethyl methacrylate, diallyl phthalate, allyl acrylate, allyl methacrylate, trimethylolpropane triacrylate, and trimethylolpropane trimethacrylate) can also be used.

The polymer particles as the matrix particle, having a mean particle size of the above-specified range, can be obtained by, for example, suspension polymerization of the above-described vinyl-based monomer or pulverization of the polymer bulk. With respect to the preparation of the matrix particle having a uniform particle size, the matrix particle can easily be produced by a swelling polymerization method as described in JP-B-57-24369, a polymerization method as described in *J. Polym. Sci., Polymer Letter Ed.*, or polymerization methods as previously proposed by the present inventors (JP-A-61-215602, JP-A-61-215603, and JP-A-61-215604).

The nuclear particle has a mean particle size of 0.4–200 µm, preferably 0.8–100 µm, and more preferably 1.0–50 µm, and a CV value of 20% or less.

In the invention, it is preferred from the standpoints of processability and lightweight properties during the compositing that the nuclear particle is made of an organic substance such as polymers. Incidentally, in the invention, the mean particle size and the particle size distribution are those as determined by randomly measuring 100 particles for the particle size on an electron microscopic photograph.

Representative magnetic substance that is used in the invention is iron oxide-based substances. Examples of the substance include ferrite represented by $MnFe_2O_4$ (Mn: Co, Ni, Mg, Cu, $Li_{0.5}$, $Fe_{0.5}$, etc.), magnetite represented by $Fe_3O_4$, and $Fe_2O_3$. It is necessary for the magnetic substance to contain either one of $Fe_2O_3$ and $Fe_3O_4$ having strong saturation magnetization and small residual magnetization.

The magnetic substance that is used in the invention has a mean particle size of preferably 1/5 or less, more preferably 1/10 or less, and most preferably 1/20 or less the mean particle size of the nuclear particle. When the mean particle size of the magnetic substance exceeds 1/5 of the mean particle size of the nuclear particle, it is difficult to form a coating layer having a uniform and sufficient thickness on the surface of the nuclear particle.

A ratio of the nuclear particle to the magnetic substance is preferably from 95/5 to 20/80 on a weight basis. When the amount of the magnetic substance is less than this range, the compositing effect becomes low. On the other hand, when it exceeds the above-specified range, the amount of the magnetic substance to the nuclear particle is too high, so that non-composited magnetic substances increase.

The magnetic substance that is used in the invention desirably has a hydrophobilized surface from the standpoints of affinity and compatibility of the nuclear particle with the monomer to be used in the subsequent step.

The hydrophobilization treatment of the surface of the magnetic substance is, for example, a method in which a compound having a part having an extremely high affinity with the magnetic substance and a hydrophobic part within the molecule is contacted with and bound to the magnetic substance. Examples of such a compound having a part having an extremely high affinity with the magnetic substance and a hydrophobic part within the molecule include silane compounds represented by silane coupling agents.

Hydrophobilizing the magnetic substance with a silane compound can produce particles for diagnostic reagent having superior chemical resistance, especially superior alkali resistance. Thus, it is possible to effectively prevent a problem that during the use as a diagnostic reagent, the magnetic substance peels apart from the nuclear particle to lower the magnetic performance, or minglement of contaminants generated by floating of the eliminated magnetic substance in the diagnostic reagent reaction mixture.

In the invention, in the case where the hydrophobilized magnetic substance can be well dispersed in, for example, toluene, it can be said that the magnetic substance is thoroughly hydrophobilized.

Examples of the silane compound represented by silane coupling agents include vinyl trichlorosilane, vinyl trimethoxysilane, vinyl tris(β-methoxyethoxy)silane, β-(3, 4-epoxycyclohexyl)ethyl trimethoxysilane, β-glycidoxypropyl trimethoxysilane, β-methacryloxypropyl trimethoxysilane, N-β-(aminoethyl) γ-aminopropylmethyl dimethoxysilane, N-β-(aminoethyl) γ-aminopropyl trimethoxysilane, dodecyl trimethoxysilane, hexyl trimethoxysilane, methyl trimethoxysilane, methyl triethoxysilane, phenyl trimethoxysilane, dodecyl trichlorosilane, hexyl trichlorosilane, methyl trichlorosilane, and phenyl trichlorosilane.

Examples of the method of binding the silane compound to the magnetic substance include a method in which the magnetic substance and the silane compound are mixed in an inorganic medium such as water or an organic medium such as alcohols, ethers, ketones, and esters, the mixture is heated with stirring, the magnetic substance is then separated by decantation or the like, and the inorganic medium or organic medium is removed by drying in vacuo. Further, the magnetic substance and the silane compound may be bound to each other by directly mixing and heating those. In those methods, the heating temperature is usually 30–100° C., and the heating time is about 0.5–2 hours. The amount of the silane compound used is appropriately deteremined depending on the surface area of the magnetic substance, and is usually 1–50 parts by weight, and preferably 2–30 parts by weight, per 100 parts by weight of the magnetic substance.

The coating layer of the magnetic substance on the surface of the nuclear particle is formed by that the nuclear particle and the magnetic substance are first mixed, thereby physically adsorbing the magnetic body onto the surface of the nuclear particle. The physical adsorption method as referred to herein means an adsorption method and a binding method, each of which is not accompanied with a chemical reaction.

For adsorbing the magnetic body on the surface of the nuclear particle, a method of realizing compositing by externally applying a physically strong force is also effective. Examples of this method include methods utilizing a mechanochemical effect, such as mortar method, automated mortar method, ball mill method, blade pressure powder compression method, and mechanofusion method; and dry impact preparation methods such as jet mill method and hybridizer method.

For achieving effectively and firmly the compositing, it is desirable that a physical adsorption force is strong. Examples of such a method include a method in which the compositing is carried out in an agitating element-equipped vessel at a peripheral velocity of the agitating element of preferably 15 m/sec or more, more preferably 30 m/sec or more, and most preferably from 40 to 150 m/sec. When the peripheral velocity of the agitating element is less than 15 m/sec, energy sufficient for forming the coating layer may be obtained. The upper limit of the peripheral velocity of the agitating element is not particularly limited, but is automatically determined according to the device used, the energy efficiency, etc.

The magnetic substance layer formed on the surface of the nuclear particle has a thickness of 0.005–20 μm, and preferably 0.01–5 μm, and the thickness is desirably uniform.

It is preferable that the surface of the nuclear particle is completely coated by the magnetic substance layer, and it is necessary that at least 90% of the surface of the nuclear particle be coated by the magnetic substance layer.

The polymer layer formed on the surface of the thus produced matrix particle (the polymer layer being hereinafter sometimes referred to as "coating polymer layer") is described below.

The polymer layer is formed by polymerizing a copolymerizable monomer as the major raw material and subsidiary raw materials to be optionally added, such as a polymerization initiator, an emulsifier, a dispersant, a surfactant, an electrolyte, a crosslinking agent, and a molecular weight regulator, in the presence of the matrix particle in the liquid. Forming the polymer layer by the polymerization in this manner makes it possible to introduce a desired functional group on the surface of the polymer layer, and superior surface processability can be realized.

Particularly preferable component of the polymer layer is vinyl-based polymers. Examples of vinyl-based monomers that are used for the production of vinyl-based polymers include aromatic vinyl monomers such as styrene, α-methylstyrene, halogenated styrenes, and divinylbenzene; vinyl esters such as vinyl acetate and vinyl propionate; unsaturated nitrites such as acrylonitrile; and ethylenically unsaturated carboxylic acid alkyl esters such as methyl acrylate, ethyl acrylate, ethyl methacrylate, butyl acrylate, butyl methacrylate, 2-ethylhexyl acrylate, 2-ethylhexyl methacrylate, lauryl acrylate, lauryl methacrylate, ethylene glycol diacrylate, ethylene glycol dimethacrylate, cyclohexyl acrylate, and cyclohexyl methacrylate. This vinyl-based polymer may be a homopolymer or a copolymer of two or more monomers selected from the above-described vinyl-based monomers.

Copolymers of the vinyl-based monomer with a conjugated diolefin (such as butadiene or isoprene), a copolymerizable monomer (such as acrylic acid, methacrylic acid, itaconic acid, maleic anhydride, crotonic acid, acrylamide, methacrylamide, diglycidyl acrylate, glycidyl methacrylate, N-methylolacrylamide, N-methylolmethacrylamide, 2-hydroxyethyl acrylate, 2-hydroxyethyl methacrylate, glycerol monoacrylate, glycerol monomtheacrylate, ethylene glycol diacrylate, ethylene glycol dimethacrylate, (meth)acrylate having 2–40 chains of polyethylene glycol or polypropylene glycol as a side chain, diallyl phthalate, allyl acrylate, allyl methacrylate, trimethylolpropane triacrylate, trimethylolpropane trimethacrylate, styrenesulfonic acid and its sodium salt, 2-acrylamide-2-methylpropanesulfonic acid and its sodium salt, and isoprenesulfonic acid and its sodium salt) or acrolein can also be used.

The polymerization initiator is preferably oil-soluble polymerization initiators from the standpoint of solubility in water. When a water-soluble polymerization initiator is used, there is the tendency to form a large quantity of new particles in which the polymerization does not occur on the surface of the composite particle but only a hydrophobic polymerizable monomer not containing a magnetic substance-coated particle is polymerized.

Examples of the oil-soluble polymerization initiator include peroxide compounds and azo compounds such as benzoyl peroxide, lauroyl peroxide, tertiary butyl peroxy-2-ethylhexanoate, 3,5,5-trimethylhexanoyl peroxide, and azobisisobutyronitrile.

Examples of the water-soluble initiator include persulfates (such as potassium persulfate, ammonium persulfate, and sodium persulfate), hydrogen peroxide, 2,2-azobis(2-aminopropane) mineral acid salts, azobiscyanovaleric acid and alkali metal salts and ammonium salt thereof. Redox initiators such as combinations of a persulfate or a hydrogen peroxide salt with sodium bisulfite, sodium thiosulfate, or ferrous chloride can also be used, and of those, persulfates are preferably used. A suitable amount of the polymerization initiator that can be used is in the range of 0.01–8% by weight based on the weight of the whole of the monomers.

The emulsifier used is anionic surfactants or nonionic surfactants that are generally used, and those can be used alone or in combination thereof. For example, examples of the anionic surfactant include anionic surfactants such as alkali metal salts of a higher alcohol sulfuric acid ester, alkali metal salts of an alkylbenzenesulfonic acid, alkali metal salts of a succinic acid dialkyl ester sulfonic acid, alkali metal salts of an alkyl diphenyl ether disulfonic acid, sulfuric acid ester salts of a polyoxyethylene alkyl (or alkyl phenyl) ether, and a formalin condensate of sodium naphthalenesulfonate. Besides those, reactive anionic surfactants such as Latemul S-180A (manufactured by Kao Corporation), Eleminol JS-S (manufactured by Sanyo Chemical Industries, Ltd.), Aqualon HS-10 (manufactured by Dai-ichi Kogyo Seiyaku Co., Ltd.), and Adeka Reasoap SE-10N (manufactured by Asahi Denka Co., Ltd.) can also be used.

Examples of the nonionic surfactant include polyoxyethylene alkyl ethers and polyoxyethylene alkyl phenyl ethers. Besides those, reactive nonionic surfactants such as Aqualon RS-20 (manufactured by Dai-ichi Kogyo Seiyaku Co., Ltd.) and Adeka Reasoap NE-20 (manufactured by Asahi Denka Co., Ltd.) can also be used.

The method of adding the monomer to the polymerization system in the formation of the polymer layer is not particularly limited, and any of enbloc addition method, divided addition method, and continuous addition method can be employed. The polymerization temperature varies depending on the kind of the polymerization initiator, but is usually 10–90° C., and preferably 30–85° C. The time required for the polymerization is usually about 1–30 hours.

Further, after formation of the polymer layer, functional groups can also be modified by a method such as alkali hydrolysis of ethylenically unsaturated carboxylic acid alkyl ester or alkali saponification of vinyl ester.

The polymer layer has a thickness of 0.005–20 μm, and preferably 0.01–5 μm. It is preferable that the magnetic substance layer is completely coated with the polymer layer.

The particles after formation of the polymer layer can directly be used as particles for diagnostic reagent. The polymer layer can be re-formed in order to form particle surface suitable as the particles for diagnostic reagent (the re-formed polymer layer is hereinafter referred to as a "recoat polymer layer"). In this embodiment, the first polymer layer can have a main object to cover the magnetic substance, and the second re-coat polymer layer can have a main object to introduce functional groups for forming the particle surface suitable as particles for diagnostic reagent. Thus, formation of the respective polymer layer can be conducted under the optimum conditions, and this is preferable as the production process of the particles for diagnostic reagent.

The formation method of the recoat polymer layer is basically the same as in the formation method of the first polymer layer. The recoat polymer layer is formed by conducting polymerization in a liquid containing the copolymerizable monomers as the main raw material and, if necessary, polymerization initiator, emulsifier, dispersant, surfactant, electrolyte, crosslinking agent, molecular weight regulator or the like, in the presence of the particles in the first polymer layer formed.

The component for the recoat polymer layer is preferably vinyl-based polymers. Examples of the vinyl-based polymer used for the production include aromatic vinyl monomers such as styrene, α-methylstyrene, halogenated styrene or divinylbenzene; vinyl esters such as vinyl acetate or vinyl propionate; unsaturated nitrites such as acrylonitrile; and ethylenically unsaturated carboxylic acid alkyl esters such as methyl acrylate, ethyl acrylate, ethyl methacrylate, butyl acrylate, butyl methacrylate, 2-ethylhexyl axrylate, 2-ethylhexyl methacrylate, lauryl acrylate, lauryl methacrylate, ethylene glycol diacrylate, ethylene glycol dimethacrylate, cyclohexyl acrylate or cyclohexyl methacrylatre. Those vinyl-based polymers may be homopolymers or copolymers comprising at least two monomers selected from the above vinyl-based monomers.

Copolymers of the above vinyl-based monomers with conjugated diolefins such as butadiene or isoprene; mono- or dicarboxylic acid compounds such as acrylic acid, methacrylic acid, itaconic acid, maleic anhydride or crotonic acid; or copolymerizable monomers such as acrylamide, methacrylamide, glycidyl acrylate, glycidyl methacrylate, N-methylol acrylamide, N-methyl methacrylamide, N-isopropyl acrylamide, 2-hydroxylmethyl acrylate, 2-hydroxymethyl methacrylate, 2-hydroxylethyl acrylate, 2-hydroxyethyl methacrylate, glycerol monoacrylate, glycerol monomethacryrate, ethylene glycol diacrylate, ethylene glycol dimethacrylate, (meth)acrylates having 2–40 chains of polyethylene glycol or polypropylene glycol as a side chain, diallyl phthalate, allyl acrylate, allyl methacrylate, trimethylolpropane acrylate, trimethylolpropane trimethacrylate, styenesulfonic acid and its sodium salt, 2-acrylamide-2-methylpropanesulfonic acid and its sodium salt, isoprenesulfonic acid and its sodium salt, can also be used.

Classifying from the standpoint of the solubility in water, oil-soluble polymerization initiators are preferable as the polymerization initiator. If water-soluble polymerization initiator is used, there is the tendency to generate a large amount of fresh particles obtained by polymerization of only hydrophobic polymerizable monomers not containing coating particles of magnetic substance, not polymerization on the surface of composite particles.

Examples of the oil-soluble polymerization initiator include persulfates such as potassium persulfate, ammonium persulfate or sodium per sulfate; hydrogen peroxide, 2,2-azobis(2-aminopropane)mineral acid salts, azobiscyanovaleric acid and its alkali metal salt, and ammonium salt. Redox initiators by a combination of persulfates or hydrogen peroxide with sodium bisulfite, sodium thiosulfate, ferrous chloride or the like can also be used. Of those, persulfates are preferably used. The proportion of those polymerization initiators is preferably in a range of 0.01–8% by weight based on the weight of the entire monomers.

The emulsifier is anionic surfactants or nonionic surfactants that are generally used, and can be used alone or as mixtures thereof. Examples of the anionic surfact include anionic surfactants such as alkali metal salts of higher alcohol sulfuric acid ester, alkali metal salts of alkylbenzenesulfonic acid, alkali metal salts of succinic acid dialkyl ester sulfonic acid, alkali metal salts of alkyldiphenyl ether disulfonic acid, sulfates of polyoxyethylene alkyl(or alkylphenyl) ether, phosphates of polyoxyethylene alkyl(or alkylphenyl) ether or formalin condensate of sodium naphthalene sulfonate; and reactive surfactants such as RATEMUL S-180A (manufactured by Kao Corp.), ELEMINOL JS-2 (manufactured by Sanyo Chemical Co.), AQUARON HS-10 (manufactured by Da-Ichi Kogyo Seiyaku Co.) and ADECA REAR SOAP SE-10N (manufactured by Asahi Denka Kogyo Co.).

Examples of the nonionic surfactants include polyoxyethyelene alkyl ester, polyoxyethylene alkyl phenyl ether, and reactive nonionic surfactants such as AQUARON RS-20 (manufactured by Dai-Ichi Kogyo Seiyaku Co.) or ADECA REAR SOAP NE-20 (manufactured by Asahi Denka Kogyo Co.).

The method of adding the monomer to a polymerization system in the formation of the recoat polymer layer is not particularly limited, and any of enbloc addition method, divided addition method and continuous addition method can be used. The polymerization temperature varies depending on the kind of the polymerization initiator used, but is generally 10–90° C., and preferably 30–85° C. The time required for polymerization is generally about 1–30 hours.

After formation of the recoat polymer layer, it is also possible to modify functional groups by a method such as alkali hydrolysis of ethylenically unsaturated carboxylic acid alkyl ester or alkali saponification of vinyl ester.

The present invention can decrease the thickness of the recoat polymer layer as compared with that of the first polymer layer, and the thickness is generally 0.005–5 $\mu$m, and preferably 0.005–1 $\mu$m.

The particles for diagnostic reagent obtained according to the process of the invention are free from elution of impurities from the particles, elution of the magnetic substance per se, or elution of impurities from the magnetic substance, and hence, are suitable as a carrier for diagnostic reagent. In the use of such a carrier for diagnostic reagent, the characteristics of the surface of the polymer layer can be selected according to the purpose.

Utilization methods as the carrier for diagnostic reagent include use for quantitative or qualitative detection in which an antigen or antibody such as proteins is bound to the particles for diagnostic reagent as obtained according to the process of the invention, and a change in turbidity of the solution by passive hemagglutination based on antigen-antibody reaction with the antigen or antibody subjective for the assay is utilized; use in which an antibody is bound to the carrier, thereby binding an antigen such as viruses, bacteria, cells, hormones, and chemical substances such as dioxins for recovery and concentration; use for recovery and detection of a nucleic acid in which a nucleic acid analog such as DNA is bound to the carrier, and hybridization of the nucleic acid is utilized, or use for recovery and detection of chemical substance such as proteins and dyes bound to a nucleic acid; use in which avidin or biotin is bound to the carrier to recover and detect a molecule containing biotin or avidin; and use as a carrier for enzyme immunoassay in which an antibody or antigen is bound to the carrier, and colorimetry or chemiluminescence is utilized. So far as the conventional diagnostic items using a 96-well plate, etc., are concerned, they can be used in an automated analyzer utilizing magnetism by using the particles for diagnostic reagent obtained according to the process of the invention. Examples of substances subjective for the assay include proteins derived from living bodies; hormones such as luteinizing hormone and thyrotropin; various cancer cells; proteins that will become cancer markers such as a prostate-specific marker and a bladder cancer marker; viruses such as hepatitis B virus, hepatitis C virus, and herpes simplex virus; bacteria such as *Neisseria gonorrhoeae* and MRSA (methicillin resistance *Staphylococcus aureus*); fungi such as *Candida fungi* and *Cryptococcus fungi*; Protozoa and parasites such as *Toxoplasma gondii*; proteins and nucleic acids as constitutional elements of these viruses, bacteria, fungi, Protozoa and parasites; environmental pollutants such as dioxins; and chemical substances such as antibiotics and medicines such as antiepileptic.

The invention will be described below in more detail with reference to the following Examples, but it should be understood that the invention is not construed as being limited thereto.

1. Preparation of Nuclear Particle

The following particles were prepared by referring to the swelling polymerization method as described in JP-B-57-24369, the polymerization method as described in *J. Polym. Sci., Polymer Letter Ed.*, or the polymerization methods as previously proposed by the present inventors (JP-A-61-215602, JP-A-61-215603, and JP-A-61-215604). Nuclear particles 1–5 fall within the scope of the invention with respect to any of the mean particle size and the CV value;

and a nuclear particle 6 is a non-uniform particle having a CV value higher than the range of the invention. The following particles were prepared by recovering only the particles by centrifugation after the polymerization, which were then washed with water, dried and pulverized.

Nuclear particle 1
  Methyl methacrylate/divinylbenzene (80/20) copolymer (mean particle size: 1.8 μm, CV value: 2.2%)
Nuclear Particle 2
  Styrene/divinylbenzene (80/20) copolymer (mean particle size: 2.1 μm, CV value: 2.3%)
Nuclear Particle 3
  Polymethyl methacrylate (mean particle size: 2.3 μm, CV value: 9.5%)
Nuclear Particle 4
  Polystyrene (mean particle size: 2.1 μm, CV value: 11.3%)
Nuclear Particle 5
  Polycyclohexyl methacrylate (mean particle size: 2.4 μm, CV value: 3.5%)
Nuclear Particle 6
  Polystyrene (mean particle size: 2.1 μm, CV value: 25.5%)

2. Preparation of Matrix Particle
Coating Method 1
  Acetone was added to an oily magnetic fluid, "FV55" (manufactured by Matsumoto Yushi-Seiyaku Co., Ltd.) to deposit and precipitate particles, which were then dried to obtain a ferrite-based superparamagnetic substance having a hydrophobilized surface (mean particle size: 0.01 μm). This superparamagnetic substance had a surface hydrophobilized with a surfactant. The resulting superparamagnetic substance was added to toluene/water (weight ratio: 1/1), and the mixture was thoroughly mixed and then allowed to stand. As a result, it was confirmed that the magnetic substance was dispersed only in toluene and that the surface was hydrophobilized.

5 g of the hydrophobilized magnetic substance was mixed with 5 g of the nuclear particle, and using a hybridization system, NHS-O Model (manufactured by Nara Machine Co., Ltd.), the mixture was treated for 3 minutes at a peripheral velocity of an impeller (agitating element) of 100 m/sec (16,200 rpm).

Coating Method 2
  Acetone was added to an oily magnetic fluid, "FV55" (manufactured by Matsumoto Yushi-Seiyaku Co., Ltd.) to deposit and precipitate particles, which were then dried to obtain a ferrite-based superparamagnetic substance having a hydrophobilized surface (mean particle size: 0.01 μm). Incidentally, this superparamagnetic substance had a surface hydrophobilized with a surfactant. In order to remove the surfactant, the magnetic substance was washed with a large quantity of a 200 mM NaOH aqueous solution, and the excessive NaOH was then removed by distilled water, followed by drying.

100 g of isobutyl trimethoxysilane was added to 10 g of the dried superparamagnetic substance and mixed at 50° C. for 8 hours to subject the surface to hydrophobilization treatment, thereby obtaining a superparamagnetic substance. This magnetic substance was recovered and dried. The resulting superparamagnetic substance was added to toluene/water (weight ratio: 1/1), and the mixture was thoroughly mixed and then allowed to stand. As a result, it was confirmed that the magnetic substance was dispersed only in toluene and that the surface was hydrophobilized.

5 g of the hydrophobilized magnetic substance was mixed with 5 g of the nuclear particle, and using a hybridization system, NHS-O Model (manufactured by Nara Machine Co., Ltd.), the mixture was treated for 3 minutes at a peripheral velocity of an impeller (agitating element) of 100 m/sec (16,200 rpm).

3. Formation of Polymer Layer
Surface Coating Polymerization 1
  30 g of the matrix particle and 900 g of a 0.5% aqueous solution of a nonionic emulsifier, "Emulgen 150" (manufactured by Kao Corporation) as a dispersant were charged in a 1-liter separable flask and thoroughly dispersed. 6 g of cyclohexyl methacrylate and 1.5 g of methacrylic acid as monomers and 0.6 g of tertiary butyl peroxy-2-ethylhexanoate (Perbutyl O, manufactured by NOF Corporation) as a polymerization initiator were added to the resulting dispersion, and the mixture was reacted at 80° C. for 8 hours under a nitrogen gas stream while stirring by an anchor type impeller at 200 rpm. The reaction mixture was cooled to room temperature, and coarse materials were removed using a 500-mesh stainless steel-made screen. Further, a non-magnetic component was removed by magnetic purification.

Surface Coating Polymerization 2
  30 g of the matrix particle and 900 g of a 0.5% aqueous solution of a nonionic emulsifier, "Emulgen 150" (manufactured by Kao Corporation) as a dispersant were charged in a 1-liter separable flask and thoroughly dispersed. 30 g of cyclohexyl methacrylate and 1.5 g of methacrylic acid as monomers and 1.5 g of tertiary butyl peroxy-2-ethylhexanoate (Perbutyl O, manufactured by NOF Corporation) as a polymerization initiator were continuously added to the resulting dispersion over 2 hours and reaction was conducted. The mixture was reacted at 80° C. for 8 hours under a nitrogen gas stream while stirring by an anchor type impeller at 200 rpm. The reaction mixture was cooled to room temperature, and coarse materials were removed using a 500-mesh stainless steel-made screen. Further, a non-magnetic component was removed by magnetic purification.

Surface Coating Polymerization 3
  The method of the surface coating polymerization 1 was repeated, except that the cyclohexyl methacrylate in the surface coating polymerization 2 was replaced by styrene.

Surface Coating Polymerization 4
  30 g of the matrix particle, 750 g of a 0.5% aqueous solution of polyvinyl alcohol (PVA) and Gosenol GL-03 (manufactured by the Nippon Synthetic Chemical Industry Co., Ltd., degree of hydrolysis: 86.5–89.0 mol %; degree of polymerization: 300–400) as a dispersant were charged in a 1-liter separable flask and thoroughly dispersed. The resulting dispersion was stirred at 60° C. by an anchor type impeller at 200 rpm under a nitrogen gas stream. A mixture of 30 g of cyclohexyl methacrylate and 1.5 g of methacrylic acid as monomers and 1.5 g of tertiary butyl peroxy-2-ethylhexanoate (Perbutyl O, manufactured by NOF Corporation) as a polymerization initiator was continuously added to the dispersion over 2 hours, and reaction was conducted. The temperature was elevated to 80° C., and the reaction was continued for 3 hours. After completion of the reaction, the reaction mixture was cooled to room temperature, and coarse materials were removed by using a 500-mesh stainless steel-made screen. Further, a non-magnetic component was removed by magnetic purification.

Surface Coating Polymerization 5
  30 g of the matrix particle, 375 g of a 0.5% aqueous solution of a nonionic emulsifier, "Emulgen 150" (manufactured by Kao Corporation) and 375 g of 0.5% aqueous solution of an anionic emulsifier, SDS (sodium lauryl sulfate) as a dispersant were charged in a 1-liter separable flask and thoroughly dispersed. The resulting dispersion was stirred at 60° C. by an anchor type impeller at 200 rpm under a nitrogen gas stream. A mixture of 30 g of cyclohexyl methacrylate, 1.5 g of methacrylic acid and 0.6 g of divinylbenzene as monomers, 150 g of an aqueous solution of Emulgen 150 as a dispersant and 1.5 g of tertiary butyl peroxy-2-ethylhexanoate (Perbutyl O, manufactured by NOF Corporation) as a polymerization initiator was continuously added to the dispersion over 2 hours, and reaction was conducted. The temperature was elevated to 80° C., and the reaction was continued for 3 hours. After completion of the reaction, the reaction mixture was cooled to room temperature, and coarse materials were removed by using a 500-mesh stainless steel-made screen. Further, a non-magnetic component was removed by magnetic purification.

Surface Coating Polymerization 6

The method of the surface coating polymerization 5 was repeated, except that the cyclohexyl methacrylate in the surface coating polymerization 5 was replaced by styrene.

Surface Coating Polymerization 7

The method of the surface coating polymerization 5 was repeated except that the methacrylic acid was replaced by acrylic acid.

Surface Coating Polymerization 8

30 g of the matrix particle and 375 g of a 0.5% aqueous solution of a nonionic emulsifier, "Emulgen 150" (manufactured by Kao Corporation) and 375 g of a 0.5% aqueous solution of an anionic emulsifier, sodium lauryl sulfate (SDS), as a dispersant were charged in a 1-liter separable flask and thoroughly dispersed. The resulting dispersion was stirred at 60° C. by an anchor type impeller at 200 rpm under a nitrogen gas stream. An emulsion prepared by emulsifying a mixture of 30 g of styrene, 1.5 g of methacrylic acid and 0.6 g of divinylbenzene as monomers, 1.5 g of tertiary butyl peroxy-2-ethylhexanoate (Perbutyl O, manufactured by NOF Corporation) as a polymerization initiator, and 75 g of a 0.5% aqueous solution of a nonionic emulsifier, "Emulgen 150" (manufactured by Kao Corporation) and 75 g of a 0.5% aqueous solution of an anionic emulsifier, sodium lauryl sulfate (SDS) as dispersants at 10° C. or lower by ultrasonic finely dispersing was continuously added to the dispersion over 2 hours to conduct reaction. The temperature was elevated to 80° C., and the reaction was continued for 3 hours. After completion of the reaction, the reaction mixture was cooled to room temperature, and coarse materials were removed using a 500-mesh stainless steel-made screen. Further, a non-magnetic component was removed by magnetic purification.

Surface Coating Polymerization 9

30 g of the polymer-coated particle as obtained in the surface coating polymerization 2 and 900 g of a 0.5% aqueous solution of a nonionic emulsifier, "Emulgen 150" (manufactured by Kao Corporation) as a dispersant were charged in a 1-liter separable flask and thoroughly dispersed. 6 g of cyclohexyl methacrylate and 1.5 g of methacrylic acid as monomers and 0.6 g of tertiary butyl peroxy-2-ethylhexanoate (Perbutyl O, manufactured by NOF Corporation) as a polymerization initiator were added to the dispersion, and the resulting mixture was react at 80° C. for 8 hours under a nitrogen gas stream while stirring by an anchor type impeller at 200 rpm. The reaction mixture was cooled to room temperature, and coarse materials were removed using a 500-mesh stainless steel-made screen. Further, a non-magnetic component was removed by magnetic purification.

Surface Coating Polymerization 10

30 g of the polymer-coated particle as obtained in the surface coating polymerization 3 and 900 g of a 0.5% aqueous solution of a nonionic emulsifier, "Emulgen 150" (manufactured by Kao Corporation) as a dispersant were charged in a 1-liter separable flask and thoroughly dispersed. 6 g of styrene and 1.5 g of methacrylic acid as monomers and 0.6 g of tertiary butyl peroxy-2-ethylhexanoate (Perbutyl O, manufactured by NOF Corporation) as a polymerization initiator were added to the dispersion, and the resulting mixture was reacted at 80° C. for 8 hours under a nitrogen gas stream while stirring by an anchor type impeller at 200 rpm. The reaction mixture was cooled to room temperature, and coarse materials were removed by using a 500-mesh stainless steel-made screen. Further, a non-magnetic component was removed by magnetic purification.

Surface Coating Polymerization 11

30 g of the polymer-coated particle as obtained in the surface coating polymerization 5 and 900 g of a 0.5% aqueous solution of a nonionic emulsifier, "Emulgen 150" (manufactured by Kao Corporation) as a dispersant were charged in a 1-liter separable flask and thoroughly dispersed. 3 g of cyclohexyl methacrylate, 0.2 g of divinylbenzene, 0.5 g of methacrylic acid and 0.5 g of polyethylene glycol (n=9) monomethacrylate as monomers and 0.6 g of tertiary butyl peroxy-2-ethylhexanoate (Perbutyl O, manufactured by NOF Corporation) as a polymerization initiator were added to the dispersion, and the resulting mixture was reacted at 80° C. for 8 hours under a nitrogen gas stream while stirring by an anchor type impeller at 200 rpm. The reaction mixture was cooled to room temperature, and coarse materials were removed by using a 500-mesh stainless steel-made screen. Further, a non-magnetic component was removed by magnetic purification.

Surface Coating Polymerization 12

30 g of the polymer-coated particle as obtained in the surface coating polymerization 8 and 900 g of a 0.5% aqueous solution of a nonionic emulsifier, "Emulgen 150" (manufactured by Kao Corporation) as a dispersant were charged in a 1-liter separable flask and thoroughly dispersed. 3 g of styrene and 0.2 g of acrylic acid as monomers and 0.6 g of tertiary butyl peroxy-2-ethylhexanoate (Perbutyl O, manufactured by NOF Corporation) as a polymerization initiator were added to the dispersion, and the resulting mixture was reacted at 80° C. for 8 hours under a nitrogen gas stream while stirring by an anchor type impeller at 200 rpm. The reaction mixture was cooled to room temperature, and coarse materials were removed by using a 500-mesh stainless steel-made screen. Further, a non-magnetic component was removed by magnetic purification.

Surface Coating Polymerization 13

30 g of the polymer-coated particle as obtained in the surface coating polymerization 8 and 900 g of a 0.5% aqueous solution of a nonionic emulsifier, "Emulgen 150" (manufactured by Kao Corporation) as a dispersant were charged in a 1-liter separable flask and thoroughly dispersed. 3 g of styrene and 0.5 g of glycidyl methacrylate as monomers and 0.6 g of tertiary butyl peroxy-2-ethylhexanoate (Perbutyl O, manufactured by NOF Corporation) as a polymerization initiator were added to the dispersion, and the resulting mixture was reacted at 80° C. for 8 hours under a nitrogen gas stream while stirring by an anchor type impeller at 200 rpm. The reaction mixture was cooled to room temperature, and coarse materials were removed by using a 500-mesh stainless steel-made screen. Further, a non-magnetic component was removed by magnetic purification.

Surface Coating Polymerization 14

30 g of the polymer-coated particle as obtained in the surface coating polymerization 8 and 900 g of a 0.5% aqueous solution of a nonionic emulsifier, "Emulgen 150" (manufactured by Kao Corporation) as a dispersant were charged in a 1-liter separable flask and thoroughly dispersed. 3 g of styrene, 0.5 g of methacrylic acid and 0.5 g of glycerol monomethacrylate as monomers and 0.6 g of tertiary butyl peroxy-2-ethylhexanoate (Perbutyl O, manufactured by NOF Corporation) as a polymerization initiator were added to the dispersion, and the resulting mixture was reacted at 80° C. for 8 hours under a nitrogen gas stream while stirring by an anchor type impeller at 200 rpm. The reaction mixture was cooled to room temperature, and coarse materials were removed by using a 500-mesh stainless steel-made screen. Further, a non-magnetic component was removed by magnetic purification.

REFERENCE EXAMPLE

Method of Simultaneously Forming a Magnetic Substance Layer and a Coating Layer by Polymerization:

Acetone was added to an oily magnetic fluid, "FV55" (manufactured by Matsumoto Yushi-Seiyaku Co., Ltd.) to deposit and precipitate particles, which were then dried. The thus obtained superparamagnetic substance powder (4.8 g) was dispersed in 420 g of 0.5% sodium lauryl sulfate, to which was then added 4.2 g of styrene. The mixture was stirred at 55° C. for 1 hour under a nitrogen gas stream by an anchor type impeller at 200 rpm. 8 g of potassium persulfate and 30 g of the nuclear particle 1 (polystyrene, mean particle size: 2.1 μm, CV value: 1.5%) dispersed in 560 g of 0.5% sodium lauryl sulfate were added to the resulting mixture. Six hours later, 4.2 g of styrene and 7 g of potassium persulfate were further added thereto, and the mixture was stirred for an additional 15 hours. The reaction mixture was cooled to room temperature, and coarse materials were removed using a 500-mesh stainless steel-made screen. Further, a non-magnetic component was removed by magnetic purification. 5 g (solids content) of the thus obtained particle was dispersed in 150 g of 0.5% sodium lauryl sulfate, and 2 g of styrene, 1 g of methacrylic acid, and 1 g of potassium persulfate were further added to the dispersion. The resulting mixture was stirred at 55° C. for 4 hours under a nitrogen gas stream by an anchor type impeller at 200 rpm. The reaction mixture was cooled to room temperature, and coarse materials were removed using a 500-mesh stainless steel-made screen. Further, a non-magnetic component was removed by magnetic purification.

EXAMPLES 1 TO 14 AND COMPARATIVE EXAMPLES 1 TO 3

The formation methods of the above nuclear particle, matrix particle and polymer were combined as shown in Table 1 (Examples) and Table 2 (Comparative Examples) to produce particles for diagnostic reagent. The resulting particles for diagnostic reagent were evaluated in the following manners.

Evaluation 1: Evaluation of Magnetic Trapping Rate

A test solution containing 1% by weight of the obtained particle for diagnostic reagent in water as a dispersing medium was prepared. 1 ml of this test solution was charged in an Eppendorf tube. Magnetism of 4,000 gausses was applied to the test solution from the lateral direction, to measure a magnetic trapping rate.

Evaluation 2: Evaluation as a Carrier for EIA

A 2.0 mg portion of each of the particles for diagnostic reagent obtained in Examples 1 to 16 and Comparative Examples 1 to 3 was taken into a test tube, to which was then added 0.5 ml of a substrate reaction mixture (o-phenylenediamine: 13 mg, 0.1M sodium phosphate buffer solution (pH: 5.0): 50 ml, 30% hydrogen peroxide: 15 μl). The mixture was reacted at room temperature for 1 hour while shielding from light. The particles were removed by centrifugation, and a supernatant was measured for absorbance (wavelength: 446 nm).

Result 1: Evaluation Result of Magnetic Trapping Rate

Any of the particles for diagnostic reagent of the Examples exhibited a magnetic trapping rate of 99% by weight or more. This is because the particle size distribution is narrow, and the magnetic responsibility is uniform.

On the other hand, any of the particles for diagnostic reagent of the Comparative Examples did not achieve a magnetic trapping rate of 99% by weight or more. This is because in Comparative Examples 1 and 2, the particle size distribution is broad, and the magnetic responsibility is non-uniform and in Comparative Example 3, the content of the magnetic substance is low as 11%.

Result 2: Evaluation Result as a Carrier for EIA

In the case where the particle is used as the carrier for EIA, it is necessary that the particle per se does not mutually react with the substrate solution and does not influence the luminescence, etc., so as to not hinder the analysis results. Any of the particles of the Examples generally had a low absorbance and did not show abnormal luminescence. This is because exposure of the magnetic substance on the particle surface or elution of the magnetic substance or iron ion from the particle is extremely low. This result reveals that in the case where these particles are used as a carrier for diagnostic reagent, since they do not adversely affect the assayed values, they are suitable.

On the other hand, Comparative Example 3 exhibited abnormally high luminescence. It may be assumed that the particle prepared in this method (Reference Example) is incomplete with respect to the coating of the magnetic substance so that the magnetic substance is exposed. This result reveals that these particles become a cause to push up the background values of the analysis, leading to a reduction of the assay sensitivity, and hence, they are not suitable as the carrier for diagnostic reagent.

TABLE 1

| Example No. | Nuclear particle No. | Coating method No. | Surface coating No. | Mean particle size (μm) | CV value (%) | Content of magnetic substance (%) | Magnetic trapping rate (% by weight) | Absorbance (OD446) |
|---|---|---|---|---|---|---|---|---|
| 1 | 3 | 2 | 1 | 2.9 | 8.1 | 43 | 99 or more | 0.051 |
| 2 | 1 | 1 | 2 | 2.2 | 9.4 | 43 | 99 or more | 0.044 |
| 3 | 1 | 1 | 3 | 2.3 | 9.1 | 44 | 99 or more | 0.047 |
| 4 | 2 | 2 | 4 | 2.6 | 9.8 | 43 | 99 or more | 0.020 |
| 5 | 1 | 1 | 5 | 2.8 | 9.9 | 43 | 99 or more | 0.020 |

TABLE 1-continued

| Example No. | Nuclear particle No. | Coating method No. | Surface coating No. | Mean particle size (μm) | CV value (%) | Content of magnetic substance (%) | Magnetic trapping rate (% by weight) | Absorbance (OD446) |
|---|---|---|---|---|---|---|---|---|
| 6 | 4 | 1 | 6 | 2.8 | 9.1 | 42 | 99 or more | 0.022 |
| 7 | 5 | 1 | 7 | 3.0 | 9.5 | 41 | 99 or more | 0.024 |
| 8 | 1 | 1 | 8 | 2.5 | 9.3 | 41 | 99 or more | 0.023 |
| 9 | 1 | 1 | 9 | 2.4 | 9.3 | 40 | 99 or more | 0.020 |
| 10 | 1 | 1 | 10 | 2.4 | 8.5 | 41 | 99 or more | 0.021 |
| 11 | 1 | 1 | 11 | 3.0 | 9.1 | 42 | 99 or more | 0.010 |
| 12 | 1 | 1 | 12 | 2.7 | 8.8 | 41 | 99 or more | 0.009 |
| 13 | 1 | 1 | 13 | 2.7 | 9.4 | 40 | 99 or more | 0.008 |
| 14 | 1 | 1 | 14 | 2.8 | 9.5 | 40 | 99 or more | 0.008 |

TABLE 2

| Comparative Example No. | Nuclear particle No. | Coating method No. | Surface coating No. | Mean particle size (μm) | CV value (%) | Content of magnetic substance (%) | Magnetic trapping rate (% by weight) | Absorbance (OD446) |
|---|---|---|---|---|---|---|---|---|
| 1 | 6 | 1 | 1 | 2.5 | 52.8 | 43 | 86 | 0.055 |
| 2 | 6 | 1 | 2 | 2.8 | 61.3 | 42 | 79 | 0.051 |
| 3 | Particle as obtained in Referential Example 1 | | | 2.4 | 5.1 | 11 | 75 | 0.331 |

According to the process of the invention, it is possible to simply and effectively prepare particles for diagnostic reagent having a uniform particle size different from the conventional methods. The particles for diagnostic reagent of the invention can be used as a biochemical carrier such as a carrier for diagnostic reagent. Further, as application examples, the particles for diagnostic reagent of the invention can be applied to use for medical diagnostic reagents, especially to particles responsible to automated assaying instruments.

It should further be apparent to those skilled in the art that various changes in form and detail of the invention as shown and described above may be made. It is intended that such changes be included within the spirit and scope of the claims appended hereto.

This application is based on Japanese Patent Application No. 2002-083733 filed Mar. 25, 2002 and No. 2002-314730 filed Oct. 29, 2002, the disclosures of which are incorporated herein by reference in their entireties.

What is claimed is:

1. A process for producing particles for diagnostic reagent, which comprises:

forming a matrix particle by mixing a nuclear particle having a CV value of 20% or less and a magnetic substance containing at least one of $Fe_2O_3$ and $Fe_3O_4$ and giving a shear force to the mixture to adsorb the magnetic substance on the surface of the nuclear particle; and polymerizing a polymerizable monomer in the presence of said matrix particle having a mean particle size of 0.4–200 μm to form a polymer layer on the magnetic substance layer.

2. The process of producing particles for diagnostic reagent as claimed in claim 1, wherein the magnetic substance has a hydrophobic surface.

3. The process of producing particles for diagnostic reagent as claimed in claim 1, wherein the magnetic substance layer has a thickness of 0.005–20 μm.

4. The process of producing particles for diagnostic reagent as claimed in claim 1, wherein the step of forming a polymer layer includes a step of dispersing the matrix particle in an aqueous medium and a step of emulsion polymerizing the polymerizable monomer in the presence of the matrix particle.

5. The process of producing particles for diagnostic reagent as claimed in claim 1, wherein the polymer layer has a thichness of 0.005–20 μm.

6. A process for producing particles for diagnostic reagent, which comprises further polymerizing a polymerizable monomer in the presence of the particles obtained by the process as claimed in claim 1 to form a polymer layer.

7. The process of claim 1, wherein said nuclear particle is a non-magnetic substance.

8. The process of claim 1, wherein said nuclear particle has a mean particle size of 0.8 to 100 μm.

9. The process of claim 1, wherein said magnetic substance has a mean particle size ⅕ or less than the mean particle size of said nuclear particle.

10. The process of claim 1, wherein a ratio of said nuclear particle to said magnetic substance is 95/5 to 20/80 on a weight basis.

11. The process of claim 1, wherein said magnetic substance has a hydrophobilized surface.

12. The process of claim 1, wherein said shear force is by a method selected from the group consisting of mechanochemical or a dry impact preparation method.

* * * * *